United States Patent
Maeda et al.

(10) Patent No.: US 11,439,473 B2
(45) Date of Patent: Sep. 13, 2022

(54) SURGICAL CONTROL APPARATUS, SURGICAL CONTROL METHOD, AND PROGRAM

(71) Applicant: SONY CORPORATION, Tokyo (JP)

(72) Inventors: Takeshi Maeda, Tokyo (JP); Seiji Wada, Kanagawa (JP); Tatsumi Sakaguchi, Kanagawa (JP); Kana Matsuura, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 30 days.

(21) Appl. No.: 15/764,916

(22) PCT Filed: Sep. 27, 2016

(86) PCT No.: PCT/JP2016/078347
§ 371 (c)(1),
(2) Date: Mar. 30, 2018

(87) PCT Pub. No.: WO2017/061294
PCT Pub. Date: Apr. 13, 2017

(65) Prior Publication Data
US 2018/0256272 A1    Sep. 13, 2018

(30) Foreign Application Priority Data
Oct. 9, 2015 (JP) .............................. JP2015-201343

(51) Int. Cl.
*G06F 3/00* (2006.01)
*A61B 34/00* (2016.01)
(Continued)

(52) U.S. Cl.
CPC .............. *A61B 34/70* (2016.02); *A61B 34/25* (2016.02); *A61B 90/361* (2016.02); *A61B 90/50* (2016.02);
(Continued)

(58) Field of Classification Search
CPC ....... A61B 34/70; A61B 34/25; A61B 90/361; A61B 90/50; G06F 3/012; G06F 3/013; G06F 3/017
(Continued)

(56) References Cited

U.S. PATENT DOCUMENTS 7,395,249 B2 * 7/2008 Wang .................... G16H 40/63
706/14
2005/0033580 A1    2/2005 Wang
(Continued)

FOREIGN PATENT DOCUMENTS

| CN | 101119680 A | 2/2008 |
| JP | 10-127565 A | 5/1998 |

(Continued)

OTHER PUBLICATIONS

International Search Report dated Dec. 6, 2016 in PCT/JP2016/078347, 1 page.

(Continued)

*Primary Examiner* — Frank F Huang
(74) *Attorney, Agent, or Firm* — Xsensus LLP

(57) ABSTRACT

The present invention relates to a surgical control apparatus, a surgical control method, and a program that can prevent erroneous operations of surgical apparatuses when the surgical apparatuses are controlled with contactless inputs.
A state estimation block (64) estimates a state of an operator recognized by a recognition block (61) on the basis of at least one type of contactless input sent from the operator. In accordance with the state estimated by the state estimation block (64), a command block (62) restricts a control operation of a surgical camera (11), a camera arm (12), or an image processing block (66) based on at least one type of contactless input sent from the operator recognized by the recognition block (61). The present invention is applicable (Continued)

to a surgical system and the like that have a surgical camera (11), a camera arm (12), an action recognition camera (13), a display (14), a control apparatus (15), a pair of glasses (17), a microphone (18), a marker, a foot switch (20), etc., thereby enabling the treatment realized by referencing images.

20 Claims, 12 Drawing Sheets

(51) Int. Cl.

| | |
|---|---|
| *G06F 3/01* | (2006.01) |
| *A61B 90/50* | (2016.01) |
| *A61B 90/00* | (2016.01) |
| *A61B 34/20* | (2016.01) |
| *A61B 17/00* | (2006.01) |

(52) U.S. Cl.
CPC .............. *G06F 3/012* (2013.01); *G06F 3/013* (2013.01); *G06F 3/017* (2013.01); *A61B 2017/00203* (2013.01); *A61B 2017/00216* (2013.01); *A61B 2034/2055* (2016.02); *A61B 2034/254* (2016.02); *A61B 2090/365* (2016.02); *A61B 2090/367* (2016.02); *A61B 2090/372* (2016.02); *A61B 2090/3937* (2016.02); *A61B 2090/502* (2016.02); *G05B 2219/35444* (2013.01)

(58) Field of Classification Search
USPC .............................................. 606/1
See application file for complete search history.

(56) References Cited

U.S. PATENT DOCUMENTS

| | | | |
|---|---|---|---|
| 2011/0026678 A1* | 2/2011 | Bonfiglio | A61B 6/00 378/114 |
| 2011/0234484 A1 | 9/2011 | Ogawa et al. | |
| 2014/0142386 A1* | 5/2014 | Ogawa | A61B 1/00039 600/118 |

FOREIGN PATENT DOCUMENTS

| | | |
|---|---|---|
| JP | 2001-299691 A | 10/2001 |
| JP | 2008529707 A | 8/2008 |
| JP | 2011-206180 A | 10/2011 |

OTHER PUBLICATIONS

Chinese Office Action dated May 28, 2020, issued in corresponding Chinese Patent Application No. 2016800574785.
Japanese Office Action dated Jun. 30, 2020, issued in corresponding Japanese Patent Application No. 2017-544454.

* cited by examiner

FIG. 4

| AUDIO | LINE OF SIGHT | HEAD MOVEMENT | GESTURE | FOOT SWITCH | COMMAND | COMMAND TYPE |
|---|---|---|---|---|---|---|
| ZOOM-IN/ZOOM-OUT | INSIDE SCREEN | – | – | – | ZOOM-IN/ZOOM-OUT AROUND LINE-OF-SIGHT POSITION | IMAGING CONTROL |
| FOCUS | INSIDE SCREEN | – | – | – | FOCUS AT LINE-OF-SIGHT POSITION | IMAGING CONTROL |
| PIVOT | NO MOVEMENT INSIDE SCREEN | TRAVEL | – | PRESS | PIVOTALLY MOVE CAMERA ACCORDING TO HEAD MOVEMENT | CAMERA ARM CONTROL |
| SLIDE | MOVEMENT IN THE SAME DIRECTION AS HEAD ROTATIONAL DIRECTION INSIDE SCREEN | ROTATION | – | PRESS | SLIDABLY MOVE CAMERA ACCORDING TO LINE-OF-SIGHT POSITION | CAMERA ARM CONTROL |
| MENU | – | – | – | PRESS | DISPLAY MENU | MENU DISPLAY CONTROL |
| ANNOTATION/POINTER | – | – | – | PRESS | DISPLAY ANNOTATION | ANNOTATION DISPLAY CONTROL |
| HANDS FREE | – | – | – | PRESS | SET HANDS-FREE MODE | MODE CONTROL |
| STOP | – | – | – | PRESS | SET MANUAL MODE | MODE CONTROL |
| – | – | – | – | LONG PRESS | SET MANUAL MODE | MODE CONTROL |
| – | OUTSIDE SCREEN | – | – | PRESS | SET MANUAL MODE | MODE CONTROL |
| – | – | – | OTHER THAN REGISTERED GESTURES | – | SET MANUAL MODE | MODE CONTROL |
| LARGER THAN PREDETERMINED VALUE | – | – | – | – | SET MANUAL MODE | MODE CONTROL |

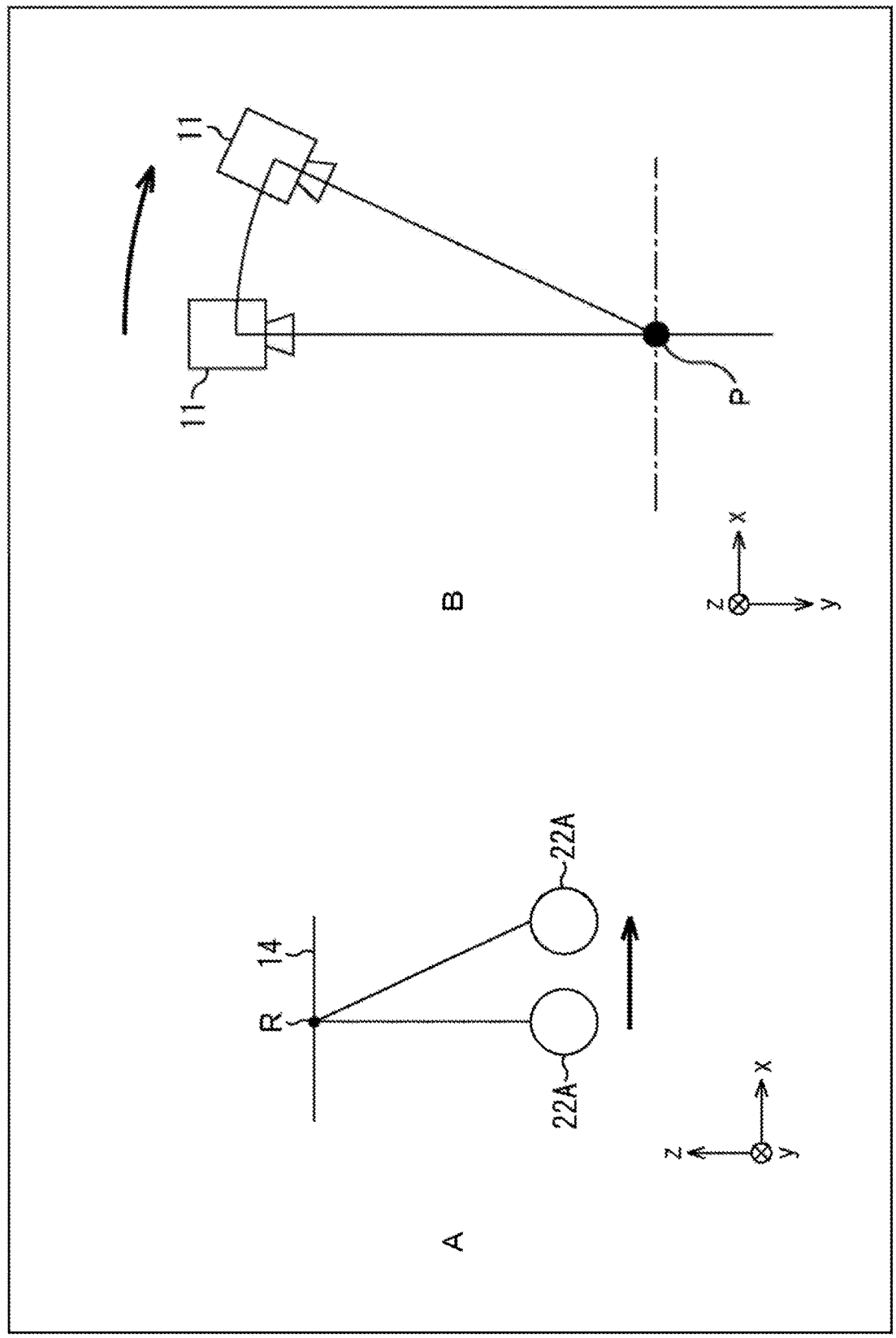

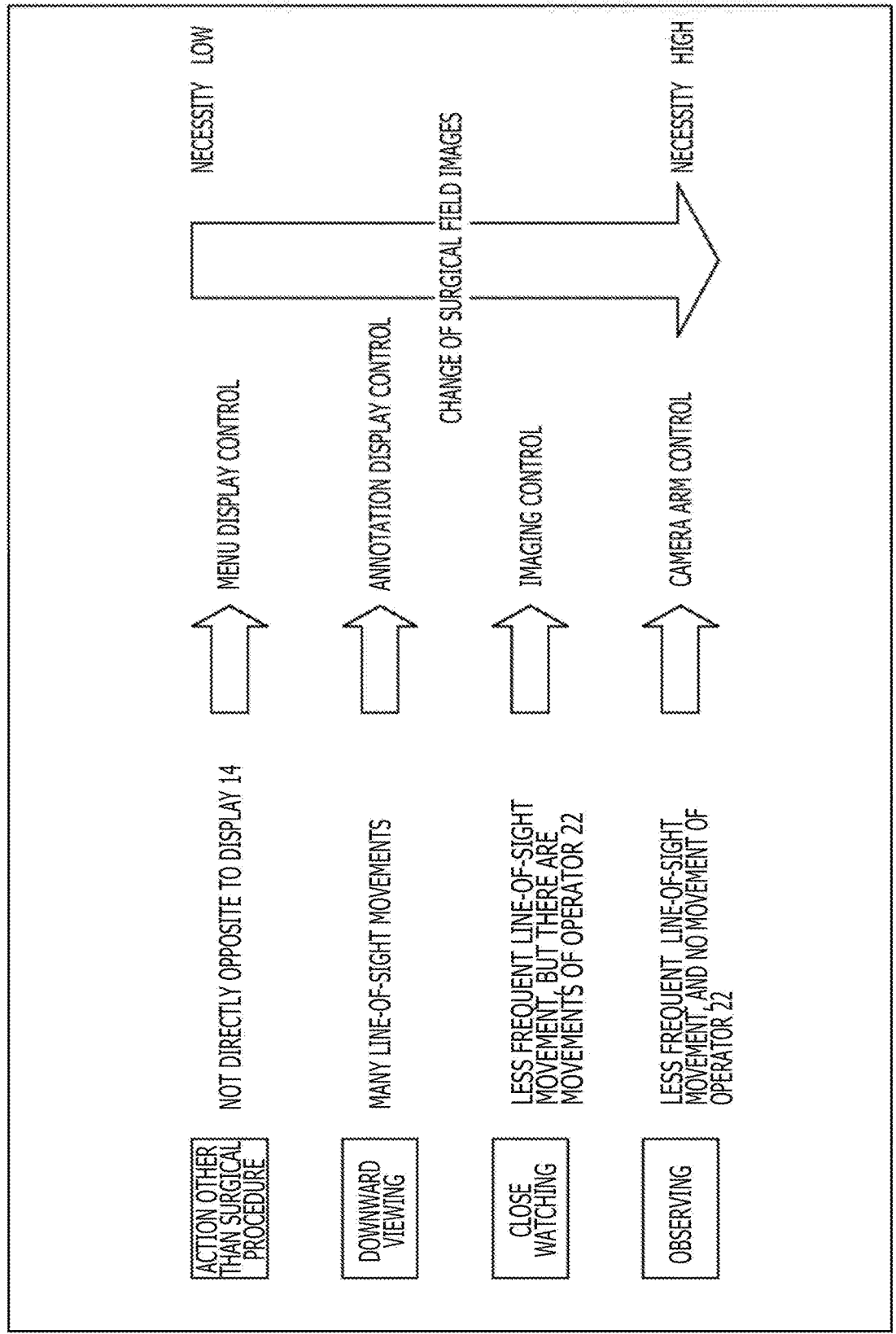

FIG. 8

| YES/NO OF DIRECTION OPPOSITION TO DISPLAY 14 | TRAVEL AMOUNT OF LINE OF SIGHT | MOVEMENT OF OPERATOR 22 | STATE | TYPE OF PERMITTED COMMANDS |
|---|---|---|---|---|
| NO | — | — | ACTION OTHER THAN SURGICAL PROCEDURE | MENU DISPLAY CONTROL |
| YES | MANY | — | DOWNWARD VIEWING | MENU DISPLAY CONTROL ANNOTATION DISPLAY CONTROL |
| YES | FEW | YES | CLOSE WATCHING | MENU DISPLAY CONTROL ANNOTATION DISPLAY CONTROL IMAGING CONTROL |
| YES | FEW | NO | OBSERVATION | MENU DISPLAY CONTROL ANNOTATION DISPLAY CONTROL IMAGING CONTROL CAMERA ARM CONTROL |

# SURGICAL CONTROL APPARATUS, SURGICAL CONTROL METHOD, AND PROGRAM

TECHNICAL FIELD

The present disclosure relates to a surgical control apparatus, a surgical control method, and a program and, more particularly, to a surgical control apparatus, a surgical control method, and a program that are configured to prevent an erroneous operation of a surgical apparatus from happening in the case where the surgical apparatus is controlled by contactless inputs.

BACKGROUND ART

A surgical system has been devised in which a surgical system controls a surgical apparatus by inputting such contactless information as voices, gestures, and lines of sight (refer to PTL 1, for example). With such a surgical system, an operator for whom the practicing of sterilization measures is essential is able to control a surgical apparatus without touching the manipulation buttons and other controls.

However, as compared with inputs by touch, contactless inputs may cause the erroneous recognition of inputs, thereby making a surgical apparatus operate in an erroneous manner. With a surgical system, any erroneous operation of a surgical apparatus affects the life of a patient, so that it is essential to prevent any erroneous operation of the surgical apparatus.

CITATION LIST

Patent Literature

[PTL 1]
U.S. Patent Application Publication No. 2011/026678

SUMMARY

Technical Problem

Therefore, in controlling surgical apparatuses by contactless inputs, the realization of fail-safe is demanded so as to prevent erroneous operations of the surgical apparatuses.

The present disclosure, executed in consideration of the above-mentioned situations, is intended to prevent erroneous operations of surgical apparatuses when surgical apparatuses are controlled by contactless inputs.

Solution to Problem

According to one aspect of the present disclosure, there is provided a surgical control apparatus. This surgical control apparatus has: a state estimation block configured to estimate, on the basis of at least one type of contactless input from a user recognized by a first contactless input recognition block, a state of the user; and a restriction block configured to restrict, in accordance with the state estimated by the state estimation block, a control operation of a surgical apparatus based on at least one type of contactless input from the user recognized by a second contactless input recognition block.

A surgical control method and a program practiced as other aspects of the present disclosure correspond to the surgical control apparatus practiced as one aspect of the present disclosure.

In one aspect of the present disclosure, on the basis of at least one type of contactless input from a user recognized by the first contactless input recognition block, a state of the user is estimated and, in accordance with the estimated state, a control operation of the surgical apparatus based on at least one type of contactless input from the user recognized by the second contactless input recognition block is restricted.

Advantageous Effects of Invention

According to one aspect of the present disclosure, a surgical apparatus can be controlled. In addition, according to another aspect of the present disclosure, an erroneous operation of a surgical apparatus can be prevented when the surgical apparatus is controlled with contactless inputs.

It should be noted that the effects described here are not necessarily restricted; namely, any of the effects described in the present disclosure may be effects denoted here.

BRIEF DESCRIPTION OF DRAWINGS

FIG. 4 is a diagram illustrating one example of a relation between input information and commands.

FIG. 5 is a diagram illustrating the description of the execution of a pivot movement command by a control block depicted in FIG. 3.

FIG. 7 is a diagram illustrating one example of a state of an operator estimated by a state estimation block depicted in FIG. 3.

FIG. 8 is a diagram for the description of a method of estimating an operator state in the state estimation block depicted in FIG. 3.

DESCRIPTION OF EMBODIMENTS

The following describes modes (hereafter referred to as embodiments) of executing the present disclosure. It should be noted that the description will be done in the following sequence.

1. First Embodiment: Surgical System (FIG. 1 through FIG. 10)
2. Second Embodiment: Surgical System (FIG. 11)
3. Third Embodiment: Computer (FIG. 12)

First Embodiment (Example of Configuration of Surgical System Practiced as First Embodiment)

Figure 1:
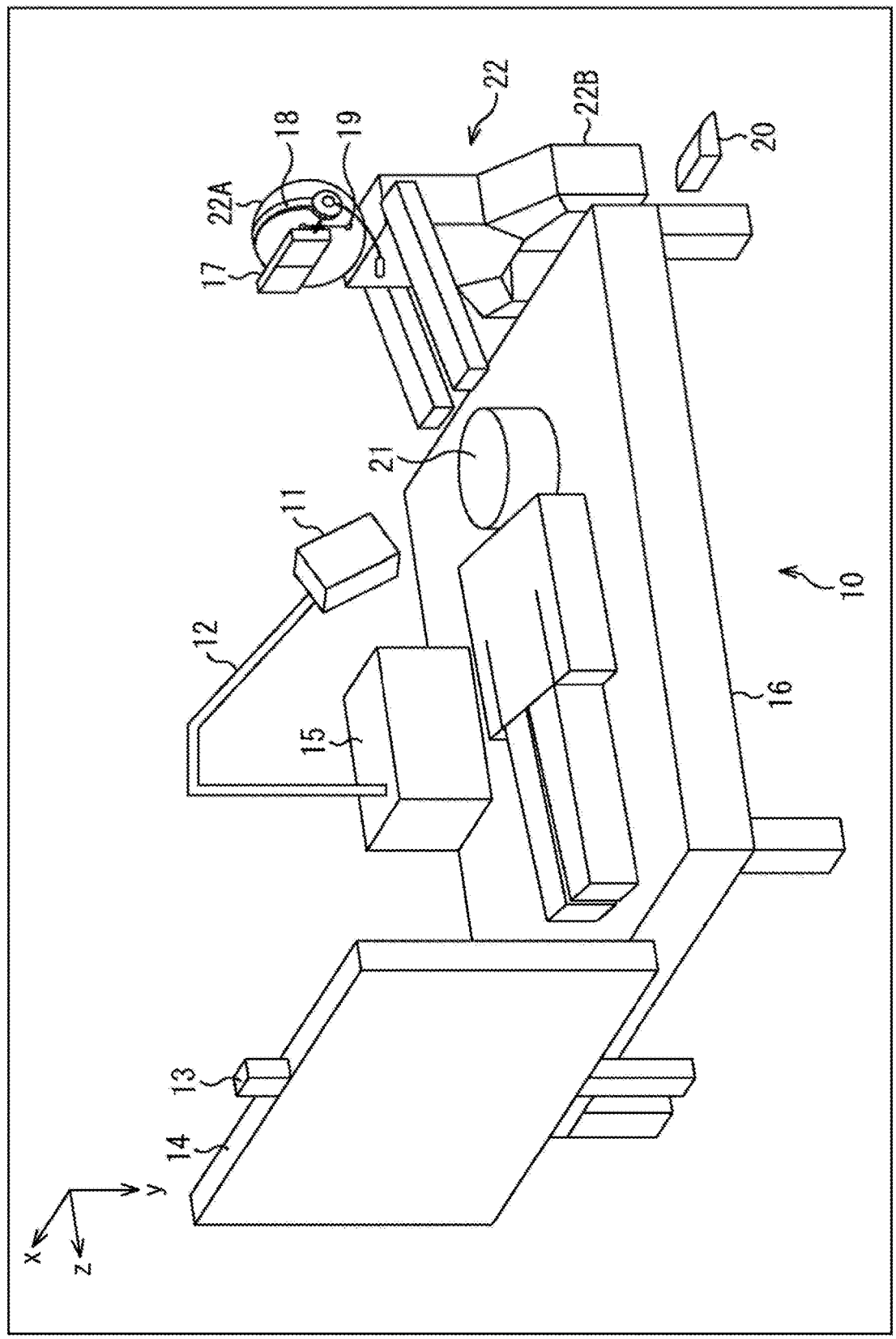
FIG. 1 is a block diagram illustrating one example of a configuration of a surgical system practiced as a first embodiment to which the present disclosure is applied.

FIG. 1 is a block diagram illustrating one example of a configuration of a surgical system practiced as a first embodiment to which the present disclosure is applied.

A surgical system 10 has a surgical camera 11, a camera arm 12, an action recognition camera 13, a display 14, a control apparatus 15, an operating table 16, surgical glasses 17, a microphone 18, a marker 19, and a foot switch 20. The surgical system 10 is arranged in an operating room or the like and enables such treatments as surgical operations and the like that reference images taken with the surgical camera 11.

To be more specific, the surgical camera 11 (a surgical imaging apparatus) of the surgical system 10 is a modality device such as a 3D camera or the like held by the camera arm 12. The surgical camera 11 takes an image of the surgical field of a patient 21 lying on the operating table 16 and transmits a resultant 3D image to the control apparatus 15 as a surgical field image. The camera arm 12 holds the surgical camera 11 so as to control the position and the angle of the surgical camera 11.

The action recognition camera 13 is a 2D camera, for example, and arranged on top of the display 14. The action recognition camera 13 takes an image of an operator 22 who wears the surgical glasses 17, the microphone 18, and the marker 19 on the head 22A. The action recognition camera 13 transmits a 2D image obtained as a result of imaging to the control apparatus 15 as an operator image.

The display 14 is a 3D display having a comparatively large screen and arranged at a position (in the example depicted in FIG. 1, a position directly opposite to the operator 22 with the operating table 16 in between) comparatively far from the operator 22. Surgical field images and the like sent from the control apparatus 15 are displayed.

The control apparatus 15 sets an operation mode to a manual mode or a hands-free mode. In the manual mode, the surgical system 10 is controlled on the basis of the input (force application to the camera arm 12 and an operation of manipulation buttons and the other controls, not depicted, installed on each of the component blocks, for example) by the hands of the operator 22. In the hands-free mode, the surgical system 10 is controlled on the basis of the contactless input of voice, line of sight, movement and direction of the head 22A, and gesture that are independent of the hands of the operator 22 and on the basis of the input by the contact of a leg 22B onto the foot switch 20.

The control apparatus 15 receives an operator image sent from the action recognition camera 13 and detects the position of the marker 19 worn on the head 22A of the operator 22 within the operator image, thereby detecting the movement of the head 22A (head tracking) and recognizing the direction of the head 22A. Further, the control apparatus 15 recognizes a gesture done by the operator 22 from the operator image.

The control apparatus 15 receives the information indicative of the direction of the line of sight of the operator 22 sent from the surgical glasses 17 and, the basis of this information and the position and direction of the head 22A, recognizes the position of the line of sight on the screen of the display 14. The control apparatus 15 receives a voice sent from the microphone 18 so as to execute voice recognition on that voice. The control apparatus 15 receives, from the foot switch 20, a manipulation signal indicative of a manipulation done on the foot switch 20 and, on the basis of that manipulation signal, recognizes the contents of the manipulation done on the foot switch 20.

Further, if the operation mode is the hands-free mode, the control apparatus 15 uses, as input information, the movement and direction of the head 22A, a gesture of the operator 22, the line-of-sight positional information indicative of the position of a line of sight on the screen of the display 14, voice recognition results, sound volume, and the manipulation information indicative of the contents of a manipulation done on the foot switch 20. On the basis of the input information, the control apparatus 15 recognizes a command from the operator 22 and a state of the operator 22.

In accordance with a state of the operator 22, the control apparatus 15 permits a command from the operator 22. In accordance with the permitted command, the control apparatus 15 controls the imaging by the surgical camera 11, controls the driving of the camera arm 12, controls the displaying of the display 14, and changes operation modes.

The surgical glasses 17 are worn around the head 22A of the operator 22 and include a 3D polarized glasses and a line-of-sight detection device. The operator 22 can look at the display 14 through the 3D polarized glasses of the surgical glasses 17, thereby recognizing a surgical field image displayed on the display 14 as a 3D image.

Further, by seeing surroundings through the surgical glasses 17, the operator 22 enters the line of sight into the surgical glasses 17. A line-of-sight device of the surgical glasses 17 detects the line of sight of the operator 22 and transmits the information indicative of the direction of the line of sight to the control apparatus 15.

The microphone 18 is worn on the head 22A of the operator 22. The microphone picks up a surrounding voice including a voice and so on of the operator 22 and transmits the picked-up voice to the control apparatus 15. The marker 19 is worn on the head 22A of the operator 22.

The foot switch 20 is arranged around the operator 22 and manipulated by the contact of the leg 22B of the operator 22. The foot switch 20 transmits a manipulation signal indicative of a manipulation done by the leg 22B of the operator 22 to the control apparatus 15.

With the surgical system 10 as described above, the operator 22 lays the patient 21 on the operating table 16 and executes treatment such as a surgical operation while looking through the surgical glasses 17 at a surgical field image and so on displayed on the display 14.

In addition, when the operation modes, the imaging conditions of the surgical camera 11, the positions and angles of the surgical camera 11, the displays of the display 14 or the like are changed, the operator 22 executes a contactless input operation or contact foot input operation. Therefore, the operator 22 is able to executes an input operation with a surgical tool, not depicted, held in the hand. It should be noted that the operator 22 need not execute sterilization processing every time the operator 22 executes an input operation.

It should also be noted that, for a line-of-sight detection method, a method of detecting the movement and direction of the head 22A and a gesture of the operator 22, and a method of obtaining voice, any method may be employed. For example, the line-of-sight detection device or the microphone 18 may be not a wearable device.

In the present description, the horizontal direction of the display 14 is referred to as x direction, the vertical direction is referred to as y direction, and the direction perpendicular to the screen of the display 14 is referred to as z direction.

(Description of Driving of Surgical Camera)

Figure 2:
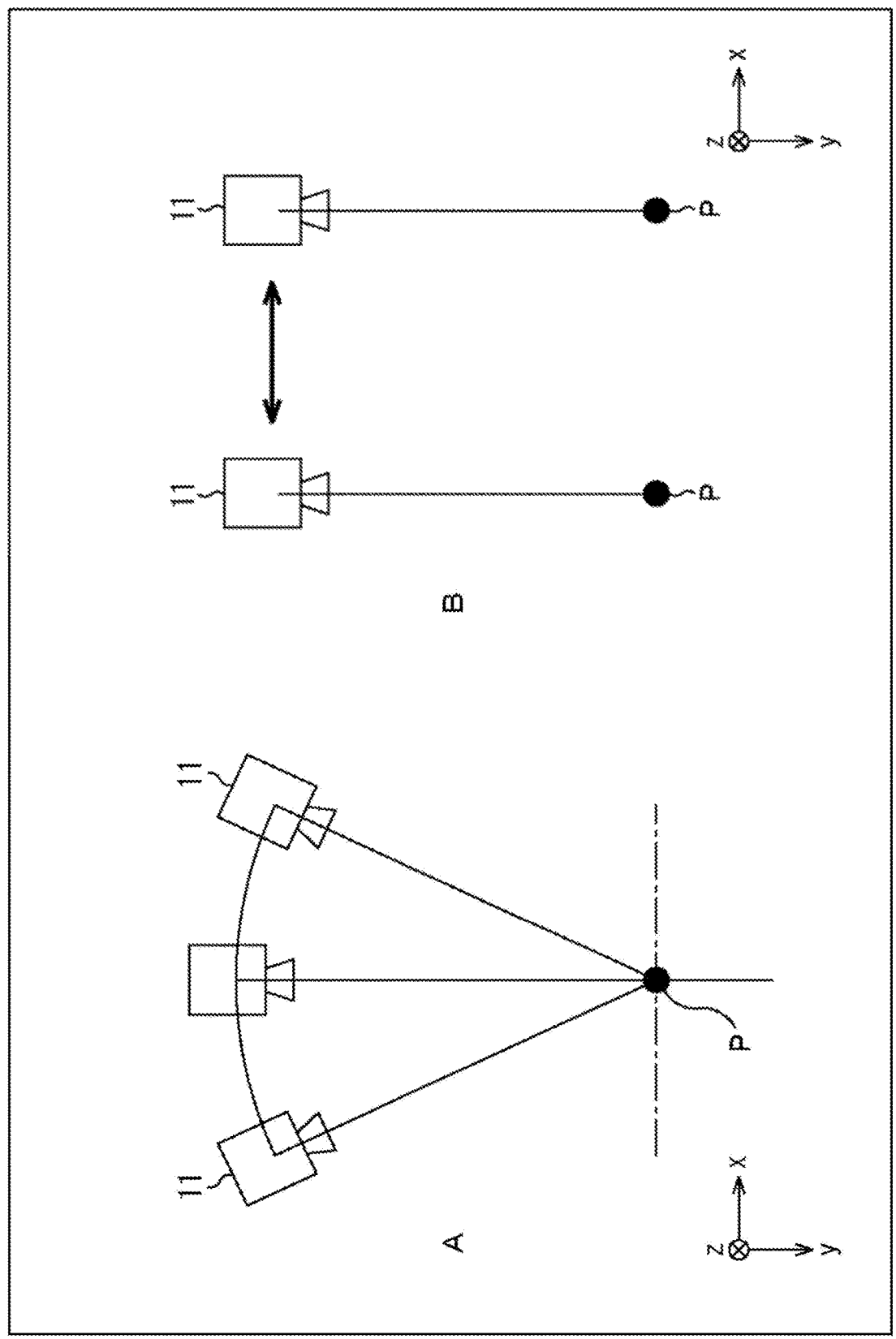
FIG. 2 is a diagram illustrating a driving operation of a surgical camera by a camera arm depicted in FIG. 1.

FIG. 2 is a diagram illustrating the driving of the surgical camera 11 by the camera arm 12 of FIG. 1.

As depicted in A of FIG. 2, the camera arm 12 can make the surgical camera 11 execute a pivot movement for changing the imaging angles without changing the imaging center. To be more specific, the camera arm 12 can move the surgical camera 11 so as to always keep constant the distance from center P of a surgical field that is a target of the imaging by the surgical camera 11. This setup allows the surgical camera 11 to take surgical field images that are same in center P of the surgical field but different in the imaging angle.

Further, as depicted in B of FIG. 2, the camera arm 12 is capable of making the surgical camera 11 execute a slide movement in the x direction in which the imaging center is moved in the x direction. Specifically, the camera arm 12 is capable of moving the surgical camera 11 in the x direction. This setup allows the surgical camera 11 to move center P of the surgical field that is a target of imaging along the x direction.

Further, although not depicted, the camera arm 12 is capable of making the surgical camera 11 execute a slide movement in the y direction or the z direction. If the surgical camera 11 executes a slide movement in the y direction, the surgical camera 11 can zoom in or zoom out an imaging range. In addition, if the surgical camera 11 executes a slide movement in the z direction, the surgical camera 11 can move center P of the surgical field along the z direction.

It should be noted that, in the present description, it is assumed that a slide movement of the surgical camera 11 be executed by the movement of the surgical camera 11 by the camera arm 12; however, it is also practicable to execute a slide movement by changing the imaging angles of the surgical camera 11 by the camera arm 12.

(Example of Configuration of Control Apparatus)

Figure 3:
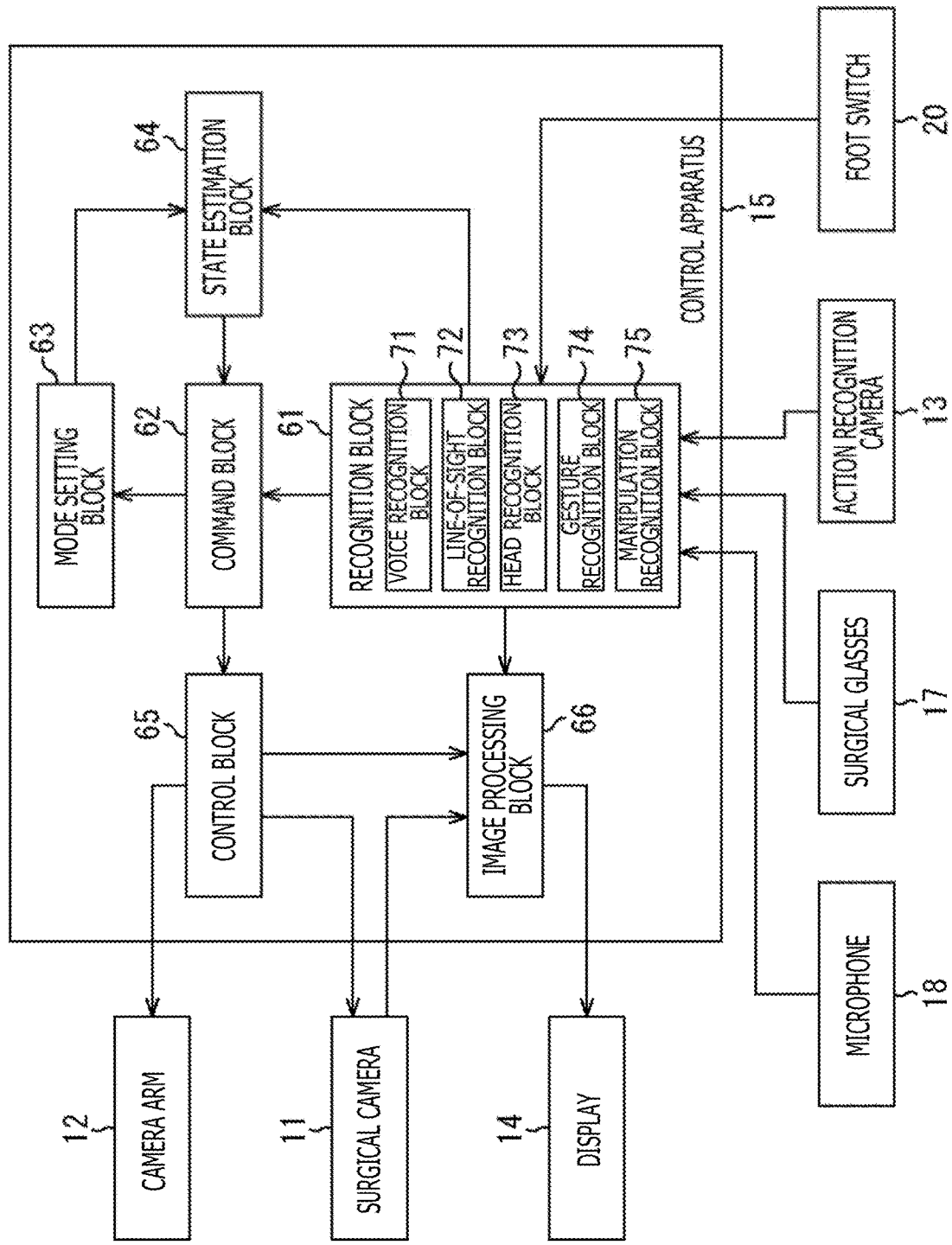
FIG. 3 is a block diagram illustrating one example of a configuration of a control apparatus depicted in FIG. 1.

FIG. 3 is a block diagram illustrating one example of the configuration of the control apparatus 15 depicted in FIG. 1.

The control apparatus 15 depicted in FIG. 3 has a recognition block 61, a command block 62, a mode setting block 63, a state estimation block 64, a control block 65, and an image processing block 66.

The recognition block 61 of the control apparatus 15 has a voice recognition block 71, a line-of-sight recognition block 72, a head recognition block 73, a gesture recognition block 74, and a manipulation recognition block 75.

The voice recognition block 71 (a contactless input recognition block) executes voice recognition on a voice sent from the microphone 18 so as to recognize a speech as the contactless input by the operator 22 (the user). In addition, the voice recognition block 71 recognizes the volume of a voice sent from the microphone 18 as the contactless input by the operator 22. The voice recognition block 71 supplies the speech and volume that are results of the voice recognition to the command block 62 as input information.

The line-of-sight recognition block 72 (a contactless input recognition block) recognizes the position of the line of sight on the screen of the display 14 as the contactless input by the operator 22 on the basis of the information indicative of the direction of line of sight sent from the surgical glasses 17 and the position and direction of the head 22A recognized by the head recognition block 73. The line-of-sight recognition block 72 supplies the line-of-sight positional information indicative of the position thereof to the command block 62, the state estimation block 64, and the image processing block 66 as input information.

The head recognition block 73 (a contactless input recognition block) detects the position of the marker 19 inside an operator image from the operator image sent from the action recognition camera 13 so as to recognize the position, movement and direction of the head 22A of the operator 22 as the contactless input by the operator 22. The head recognition block 73 supplies the movement and direction of the head 22A to the command block 62 and the state estimation block 64 as input information. In addition, the head recognition block 73 supplies the position and direction of the head 22A to the line-of-sight recognition block 72.

The gesture recognition block 74 (a contactless input recognition block) recognizes, as the contactless input from the operator 22, the input of a gesture done by the operator 22 from an operator image sent from the action recognition camera 13. The gesture recognition block 74 supplies the gesture done by the operator 22 to the command block 62 as input information.

The manipulation recognition block 75 (a contact input recognition block) receives a manipulation signal sent from the foot switch 20 and recognizes the contents of the manipulation done on the foot switch 20 as the contact input from the operator 22. The manipulation recognition block 75 supplies the manipulation information indicative of the contents of that manipulation to the command block 62 as input information.

On the basis of the input information supplied from the recognition block 61, the command block 62 recognizes a command issued from the operator 22. If the recognized command is a command for changing operation modes, then the command block 62 notifies the mode setting block 63 of that command.

On the other hand, if the recognized command issued from the operator 22 is not a command for changing operation modes, then the command block 62 (a restriction block) restricts the command issued from the operator 22 in accordance with a state supplied from the state estimation block 64. That is, in accordance with the state supplied from the state estimation block 64, the command block 62 permits a predetermined command issued from the operator 22. The command block 62 supplies the permitted command to the control block 65.

In accordance with a command supplied from the command block 62, the mode setting block 63 sets the operation mode to the manual mode or the hands-free mode. The mode setting block 63 supplies the set mode to the state estimation block 64.

If the operation mode supplied from the mode setting block 63 is the hands-free mode, the state estimation block 64 estimates a state of the operator 22 on the basis of the input information supplied from the recognition block 61. The state estimation block 64 notifies the command block 62 of the estimated state.

The control block 65 executes the command supplied from the command block 62. To be more specific, if the command supplied from the command block 62 is a command associated with the imaging control of the surgical camera 11, then the control block 65 executes imaging control of the surgical camera 11 (the surgical apparatus) in accordance with that command.

If the command supplied from the command block 62 is a command associated with the driving control of the camera arm 12, then control block 65 executes driving control of the camera arm 12 (the surgical apparatus) in accordance with that command. Further, if the command supplied from the command block 62 is a command associated with the display control of the display 14, then the control block 65 controls the image processing block 66 (the surgical apparatus) by supplying that command to the image processing block 66.

The image processing block 66 processes a surgical field image sent from the surgical camera 11. To be more specific, the image processing block 66 supplies a surgical field image sent from to the surgical camera 11 to the display 14 without change, thereby displaying that surgical field image.

Further, if the command supplied from the control block 65 is an annotation display command, then the image processing block 66 superimposes a mark (a predetermined image) on the position corresponding to the line of sight of the operator 22 inside the surgical field image sent from the surgical camera 11 on the basis of the line-of-sight positional information supplied from the line-of-sight recognition block 72. Next, the image processing block 66 supplies the surgical field imaged superimposed with the mark to the display 14, thereby displaying that surgical field image.

In addition, if the command supplied from the control block 65 is a menu display command for displaying GUI (Graphical User Interface) such as menu buttons onto the display 14, then the image processing block 66 superimposes a surgical field image sent from the surgical camera 11 with a GUI image. The image processing block 66 supplies the surgical field image superimposed with the GUI to the display 14, thereby displaying that surgical field image.

(Example of Relation Between Input Information and Commands)

FIG. 4 is a diagram illustrating one example of a relation between input information and commands.

As depicted in FIG. 4, if the voice recognition result in the input information is "zoom-in" and the line-of-sight positional information is indicative of a position inside the screen of the display 14, then the command block 62 recognizes that the command from the operator 22 is a command (hereafter referred to as a zoom-in imaging command) for having the surgical camera 11 zoom in around a subject corresponding to the line-of-sight position indicated in the line-of-sight positional information.

Likewise, if the voice recognition result in the input information is "zoom-out" and the line-of-sight positional information is indicative of a position inside the screen of the display 14, then the command block 62 recognizes that the command from the operator 22 is a command (hereafter referred to as a zoom-out imaging command) for having the surgical camera 11 zoom out around a subject corresponding to the line-of-sight position indicated in the line-of-sight positional information.

If the voice recognition result in the input information is "focus" and the line-of-sight positional information is indicative of a position inside the screen of the display 14, then the command block 62 recognizes that the command from the operator 22 is a command (hereafter referred to as a focus control command) for executing focus control of the surgical camera 11 such that the subject corresponding to the line-of-sight position indicated by the line-of-sight positional information is focused.

It should be noted that a zoom-in imaging command, a zoom-out imaging command, and a focus control command are commands associated with the imaging control of the surgical camera 11, so that these types of command are classified into "imaging control."

As described above, the operator 22 is able to enter the contents of imaging control with a voice suited for command input and enter a position necessary for imaging control with the line of sight suited for positional input. Therefore, the operator 22 can easily execute commands associated with imaging control.

Further, if the voice recognition result in the input information is "pivot," the line-of-sight positional information is indicative of a position inside the screen of the display 14, the line-of-sight positional information does not change with time, the movement of the head 22A is travel, and the manipulation information is indicative of the pressing of the foot switch 20, then the command block 62 recognizes that the command from the operator 22 is a command (hereafter referred to as a pivot movement command) for controlling the camera arm 12 such that the surgical camera 11 pivotally moves in accordance with the movement of the head 22A.

If the voice recognition result in the input information is "slide," the movement of the head 22A is rotation, the line-of-sight positional information is indicative of a position inside the screen of the display 14, the direction in the temporal change of the position indicated by the line-of-sight positional information is the same as the rotational direction of the head 22A, and the manipulation information is indicative of the pressing of the foot switch 20, then the command block 62 recognizes that the command from the operator 22 is a command (hereafter referred to as a slide movement command) for controlling the camera arm 12 such that the surgical camera 11 slides in accordance with the position of the line of sight.

It should be noted that a pivot movement command and a slide movement command are commands associated with the driving control of the camera arm 12, so that these types of commands are classified into "camera arm control."

As described above, if a combination of two or more pieces of input information does not satisfy the conditions, then the command block 62 does not recognize any such commands that for changing surgical field images as of "imaging control" type or "camera arm control" type as commands issued from the operator 22.

For example, even if the voice recognition result in the input information is "zoom-in" ("zoom-out" or "focus"), but the line-of-sight positional information is not indicative of a position inside the screen, the command block 62 determines that the recognition done is erroneous, thereby not recognizing that the command from the operator 22 is a zoom-in imaging command (a zoom-out imaging command or a focus control command).

Conversely, even if the line-of-sight positional information in the input information is indicative of a position inside the screen, but the voice recognition result is not "zoom-in" ("zoom-out" or "focus"), the command block 62 determines the recognition done is erroneous, thereby not recognizing that the command from the operator 22 is a zoom-in imaging command (a zoom-out imaging command or a focus control command).

Even if the voice recognition result in the input information is "focus," the line-of-sight positional information is indicative of a position inside the screen, the movement of the head 22A is travel, and the manipulation information is indicative of the pressing of the foot switch 20, but the line-of-sight positional information is indicative of temporal change, then the command block 62 determines that the recognition done is erroneous, thereby not recognizing that the command from the operator 22 is a pivot movement command.

Further, even if the voice recognition result in the input information is "focus," the line-of-sight positional information is indicative of a position inside the screen, the movement of the head 22A is travel, and the line-of-sight positional information does not temporarily change, but the manipulation information does not indicate that the foot switch 20 is pressed, then the command block 62 determines that the recognition done is erroneous, thereby not recognizing that the command from the operator 22 is a pivot movement command.

Therefore, a recognition hit ratio of commands that change surgical field images and therefore greatly affect surgical operations can be enhanced. Consequently, the safety of surgery can be enhanced.

In addition, a command of which type is "camera arm control" that greatly changes the contents of a surgical field image affects the surgery more than a command of which type is "imaging control." Therefore, in the example depicted in FIG. 4, the number of pieces of input information under recognition conditions of a command of which type is "camera arm control" is greater than the number of pieces of input information under recognition conditions of a command of which type is "imaging control" by 3 to 2.

It should be noted that a condition that manipulation information is indicative of the pressing of the foot switch 20 may be added to the recognition conditions of a command of which type is "imaging control," thereby increasing the number of pieces of input information under the recognition information to 3.

If the voice recognition result in the input information is "menu" and the manipulation information is indicative of the pressing of the foot switch 20, then the command block 62 recognizes that the command from the operator 22 is a menu display command. It should be noted that a menu display command is a command associated with the display control of GUI such as menu buttons and other controls of the image processing block 66 (the display control apparatus), so that the type of a menu display command is classified into "menu display control."

Further, if the voice recognition result in the input information is "annotation" or "pointer" and the manipulation information is indicative of the pressing of the foot switch 20, then the command block 62 recognizes that the command from the operator 22 is an annotation display command for displaying, as an annotation, a mark at a position corresponding to the line of sight of the operator 22 inside the screen of the display 14. It should be noted that an annotation display command is a command associated with the display control of an annotation of the image processing block 66, so that the type of an annotation command is classified into "annotation display control."

In addition, if the voice recognition result in the input information is "hands-free" and the manipulation information is indicative of the pressing of the foot switch 20, then the command block 62 recognizes that the command from the operator 22 is a command (hereafter referred to as a hands-free mode command) for setting the operation mode to the hands-free mode.

If the voice recognition result in the input information is "stop" and the manipulation information is indicative of the pressing of the foot switch 20, then the command block 62 recognizes that the command from the operator 22 is a command (hereafter referred to as a manual mode command) for setting the operation mode in a normal state to the manual mode.

As described above, when the operator 22 enters a speech associated with a menu display command, an annotation display command, or a manual mode command into the microphone 18 and executes an enter manipulation by pressing the foot switch 20, the command block 62 recognizes the entered command.

Further, if the manipulation information in the input information is indicative of the long pressing of the foot switch 20, then the command block 62 recognizes that the command from the operator 22 is a manual mode command in a normal state. If the position indicated by the line-of-sight positional information in the input information is outside the screen of the display 14 and the manipulation information is indicative of the pressing of the foot switch 20, then the command block 62 recognizes that the command from the operator 22 is a manual mode command in a normal state.

In addition, if the gesture of the operator 22 in the input information is other than a registered gesture or the sound volume in the input information is greater than a predetermined value, then the command block 62 recognizes that the command is a manual mode command in an emergency state. An emergency state denotes a state in which the hands-free mode must be stopped in emergency due to an erroneous operation or the like.

It should be noted that conditions of recognizing a manual mode command in an emergency state may be other than that the gesture of the operator 22 is a registered gesture or other than that the sound volume is greater than a predetermined value if these recognition conditions are other than the recognition conditions of the other commands.

A hands-free mode command and a manual mode command are commands associated with the control of the operation mode of the control apparatus 15, so that the types of these commands are classified into "mode control."

It should be noted that the relation between input information and commands is not restricted to the above-mentioned example depicted in FIG. 4.

That is, if the operator 22 can enter the input contents necessary for command recognition by use of a voice and a sound volume, a line of sight, a movement and direction of the head 22A, a gesture, or the manipulation of the foot switch 20 that are suited for the type of these input contents, the recognition conditions are not restricted to particular ones. In the example depicted in FIG. 4, for example, the number of types of input information for contactless input in the case of command recognition conditions that the types are "menu display control," "annotation display control," and "mode control" is one; however, the number of input information types may be more than one.

Further, a command to be recognized by the command block 62 may be any command as far as the command is for controlling each block of the surgical system 10. For example, the command block 62 may recognize a command for setting a various types of parameters of the surgical camera 11.

(Explanation of Execution of Pivot Movement Command)

FIG. 5 is a diagram illustrating the execution of a pivot movement command by the control block 65 depicted in FIG. 3.

It should be noted that A of FIG. 5 is a diagram illustrating the head 22A and the display 14 as viewed in the y direction. B of FIG. 5 is a diagram illustrating the surgical camera 11 as viewed in a direction between the z direction and the y direction.

As depicted in A of FIG. 5, when the operator 22 utters a voice "pivot" and the line of sight of the operator 22 is positioned at position R inside the screen of the display 14, if the operator 22 shifts only the head 22A in the x direction without moving the line-of-sight position on the screen while pressing the foot switch 20, then the command block 62 recognizes a pivot movement command.

If a pivot movement command is supplied from the command block 62, the control block 65 driving-controls the camera arm 12 to cause the surgical camera 11 to do a pivot movement in the x direction by an amount corresponding to a travel amount of the head 22A. Consequently, as depicted in B of FIG. 5, the surgical camera 11 travels by an amount corresponding to a travel amount of the head 22A in the x direction without changing a distance from center P.

(Explanation of Execution of Slide Movement Command)

Figure 6:
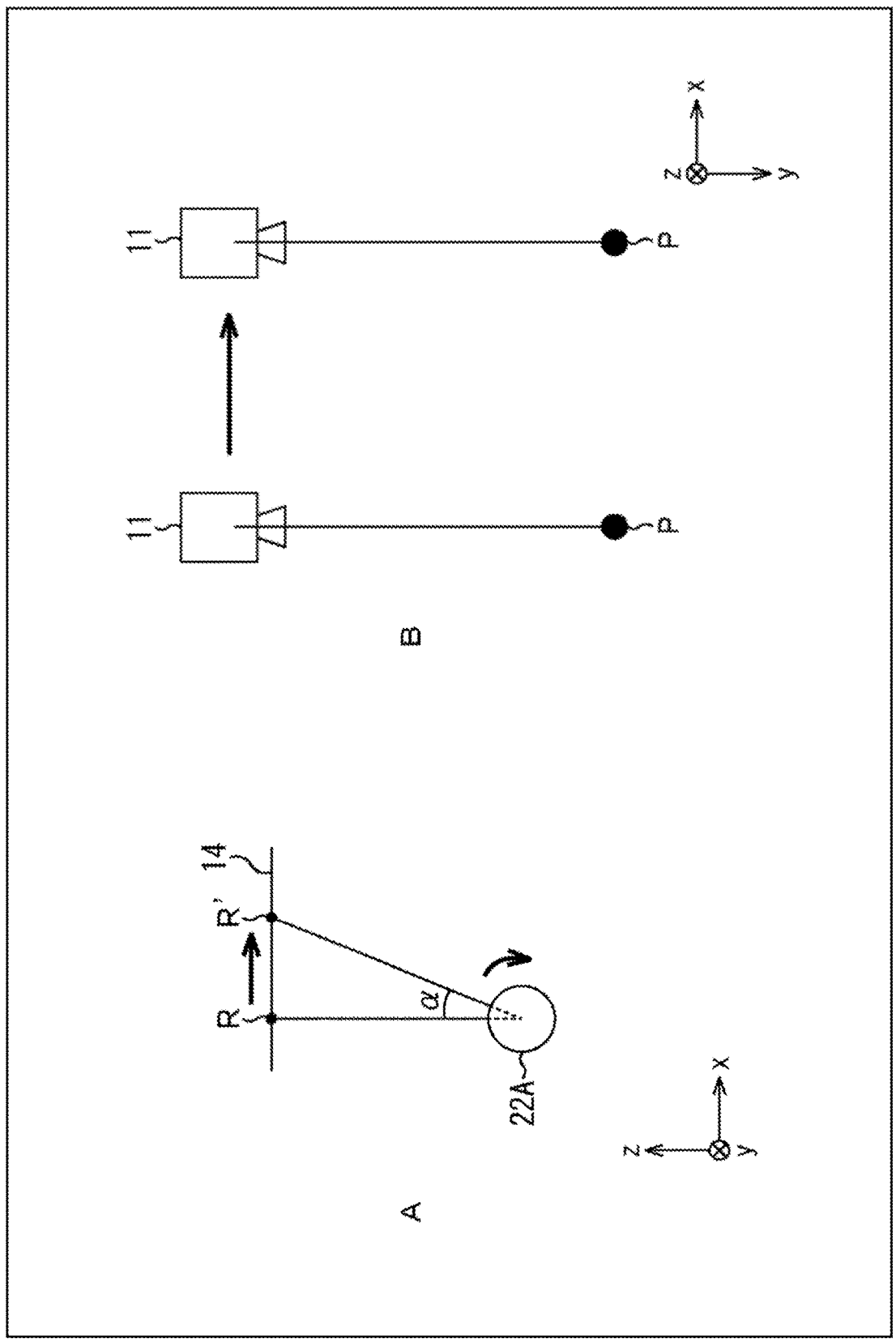
FIG. 6 is a diagram for the description of the execution of a slide movement command by a control block depicted in FIG. 3.

FIG. 6 is a diagram illustrating the execution of a slide movement command by the control block 65 depicted in FIG. 3.

It should be noted that A of FIG. 6 is a diagram illustrating the head 22A and the display 14 as viewed in the y direction while B of FIG. 6 is a diagram illustrating the surgical camera 11 as viewed from the z direction.

As depicted in A of FIG. 6, when the operator 22 utters a voice "pivot" and the line of sight of the operator 22 is positioned at position R inside the screen of the display 14, if the operator 22 causes the head 22A to rotate by angle α in a right direction so as to move the line-of-sight position on the screen in the x direction while pressing the foot switch 20, then the command block 62 recognizes a slide movement command.

If a slide movement command is supplied from the command block 62, the control block 65 driving-controls the camera arm 12 so as to cause the surgical camera 11 to slide in the x direction, thereby placing a subject corresponding to position R' of the line of sight on the screen after the movement to the center of imaging. Consequently, center P of the surgical field that is an imaging target of the surgical camera 11 travels in the x direction.

It should be noted that the control block 65 may control the speed of a slide movement in accordance with a rotational speed of the head 22A.

(Example of Estimated Operator States)

FIG. 7 is a diagram illustrating an example of states of the operator 22 that are estimated by the state estimation block 64 of FIG. 3.

As depicted in FIG. 7, the state estimation block 64 estimates that the operator 22 is in an action-other-than-surgical-procedure state, a downward viewing state, a close watching state, or an observing state.

The action-other-than-surgical-procedure state denotes a state in which the operator 22 is executing an action other than a surgical procedure (for example, checking the hand holding forceps or understanding a situation of assistants and staffs around). In the action-other-than-surgical-procedure state, it is assumed that the operator 22 be not directly opposite to the display 14. Therefore, there is no need for changing surgical field images. Consequently, if the state of the operator 22 is estimated to be the action-other-than-surgical-procedure state, the command block 62 restricts the command from the operator 22 other than a command of which type is "mode control" that changes operation modes to the command of which type is "menu display control" that does not change surgical field images.

The downward viewing state denotes a state in which the operator 22 is overlooking the surgical field in order to check for a tissue damage or bleeding, for example. In the downward viewing state, it is assumed that the line of sight of the operator 22 be frequently moving inside the screen of the display 14. In addition, in the downward viewing state, it is possible for the operator 22 to indicate a predetermined position within the surgical field image to surrounding assistants or staffs. Therefore, if the state of the operator 22 is estimated to be the downward viewing state, the command from the operator 22 other than a command of which type is "mode control" to a command of which type is "menu display control" and a command of which type is "annotation display control" that superimposes an annotation on a surgical field image.

The close watching state is a state in which the operator 22 is executing a surgical operation while closely watching a single point inside a surgical field image. In the close watching state, the line of sight of the operator 22 is inside the screen of the display 14 and the movement of the line of sight of the operator 22 is less frequent, but the operator 22 is assumed to be moving. In the close watching state, it is not necessary for the operator 22 to change the contents of a surgical field image but the operator 22 must look at the surgical field image taken under the imaging conditions suited for the surgical procedure. Therefore, if the state of the operator 22 is estimated to the close watching state, then the command block 62 restricts the command from the operator 22 other than a command of which type is "mode control" to the commands of which types are "menu display control" and "annotation display control" and a command of which type is "imaging control" that changes imaging conditions.

The observation state is a state in which the operator 22 temporarily interrupts the surgical procedure so as to observe the patient 21 for an important treatment. In the observation state, it is assumed that the line of sight of the operator 22 be inside the screen of the display 14 and the movement of the line of sight of the operator 22 and the movement of the operator 22 be less frequent. In the observation state, it is necessary for the operator 22 to observe a surgical field from various directions, so that the contents of a surgical field image must be changed.

Consequently, if the state of the operator 22 is assumed to be the observation state, the command block 62 permits all of the commands from the operator 22 other than the commands of which type is "mode control." That is, the command block 62 permits only the commands of which types are "menu display control," "annotation display control," and "imaging control" but also the commands of which type is "camera arm control" that changes the positions of the surgical camera 11.

As described above, the degree of the necessity for changing surgical field images increases from the action other than surgical procedure state to the downward viewing state to the close watching state to the observation state in this order.

It should be noted here that it is assumed that, in a state higher in the necessity for changing surgical field images, all of the commands that are permitted in the lower states be permitted; however, it is also practicable to determine the commands to be permitted for each of these states.

For example, if the state of the operator 22 is the action-other-than-surgical-procedure state, the downward viewing state, the close watching state, or the observation state, then only the commands of which type is "menu display control," "annotation display control," "imaging control," or "camera arm control" may be permitted.

(Explanation of Method of Estimating Operator State)

FIG. 8 is a diagram illustrating a method of estimating a state of the operator 22 in the state estimation block 64 depicted in FIG. 3.

On the basis of the direction of the head 22A or the line-of-sight positional information in the input information, the state estimation block 64 determines whether the operator 22 is directly opposite to the display 14.

To be more specific, if the direction of the head 22A is in the direction of the display 14, the state estimation block 64 determines that the operator 22 is directly opposite to the display 14; if the direction of the head 22A is not in the direction of the display 14, the state estimation block 64 determines that the operator 22 is not directly opposite to the display 14.

Alternatively, if the position indicated by the line-of-sight positional information is inside the screen of the display 14, the state estimation block 64 determines that the operator 22 is directly opposite to the display 14; if the position indicated by the line-of-sight positional information is outside the screen of the display 14, the state estimation block 64 determines that the operator 22 is not directly opposite to the display 14.

If the travel amount is greater than a predetermined value on the basis of the travel amount within a predetermined time of a position indicated by the line-of-sight positional information, the state estimation block 64 determines the that travel amount of the line of sight is high; if the travel amount is less than the predetermined value, the state estimation block 64 determines that the travel amount of the line of sight is low.

Further, if the amount of movement of the head 22A is greater than a predetermined value within a predetermined time on the basis of the movement of the head 22A, the state estimation block 64 determines that the operator 22 is moving; if the amount of movement of the head 22A is less than the predetermined value, the state estimation block 64 determines that the operator 22 is not moving.

It should be noted that it is also practicable that the recognition block 61 recognizes the movement of a part other than the head 22A of the operator 22 and, on the basis of the movement of the part other than the head 22A of the operator 22, the state estimation block 64 determines whether the operator 22 is moving or not. In this case, if the amount of movement of the part other than the head 22A of the operator 22 within a predetermined time is greater than a predetermined value, then the recognition block 61 determines that the operator 22 is moving; if the amount of movement of the part other than the head 22A of the operator 22 is less than the predetermined value, the recognition block 61 determines that the operator 22 is not moving.

As depicted in FIG. 8, if the operator 22 is found to be not directly opposite to the display 14, the state estimation block 64 estimates that the state of the operator 22 is the action-other-than-surgical-procedure state. In this case, the type other than "mode control" of commands from the operator 22 that are permitted is "menu display control."

Also, if the operator 22 is found to be directly opposite to the display 14 and the travel amount of the line of sight is high, then the state estimation block 64 estimates that the state of the operator 22 is the downward viewing state. In this case, the types of permitted commands other than "mode control" are "menu display control" and "annotation display control."

Further, if the operator 22 is found to be directly opposite to the display 14, the travel amount of the line of sight is found to be low, and the operator 22 is found to be moving, then the state estimation block 64 estimates that the state of the operator 22 is the close watching state. In this case, the types of permitted commands other than "mode control" are "menu display control," "annotation display control," and "imaging control."

In addition, if the operator 22 is found to be not directly opposite to the display 14, the travel amount of the line of sight is found to be low, and the operator 22 is found to be not moving, then the state estimation block 64 estimates that the state of the operator 22 is the observation state. In this case, the types of permitted commands other than "mode control" are "menu display control," "annotation display control," "imaging control," and "camera arm control."

It should be noted that, since the operator 22 executes a surgical procedure by use of forceps and the like while looking at the display 14, the frequency of the movement of the head 22A of the operator 22 during a surgical procedure is very low, but the frequency of the movement of the hands is high. Therefore, if not in the case where the amount of the movement of the head 22A is greater than a predetermined value but the amount of the movement of the head 22A is less than the predetermined value and the amount of the movement of other than the head 22A is greater than the predetermined value, the state estimation block 64 may determine that the state of the operator 22 is the close watching state.

(Explanation of Processing by Surgical System)

Figure 9:
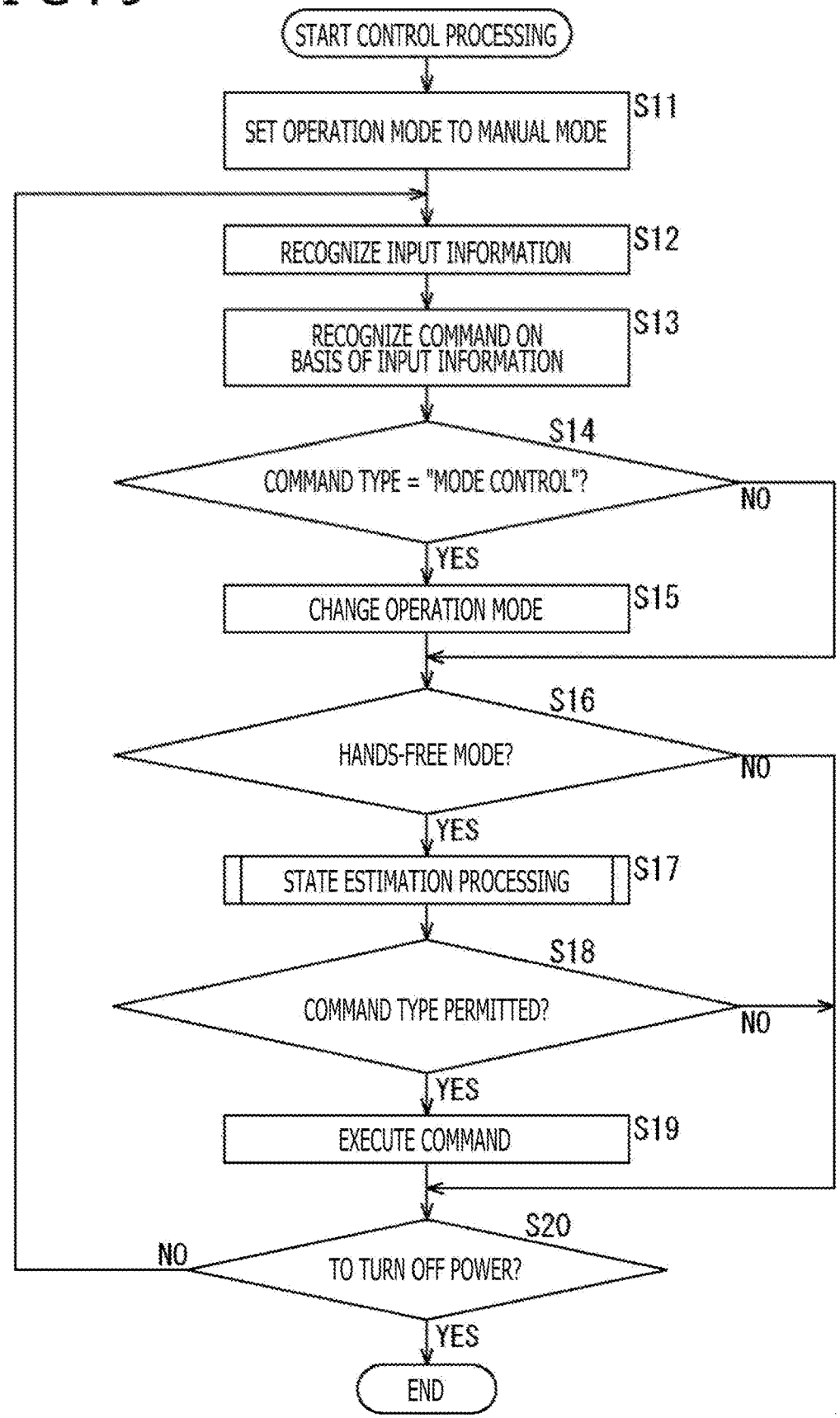
FIG. 9 is a flowchart indicative of control processing to be executed by the control apparatus of the surgical system depicted in FIG. 1.

FIG. 9 is a flowchart indicative of the control processing to be executed by the control apparatus 15 of the surgical system 10 depicted in FIG. 1. This control processing starts when the power to the control apparatus 15 is turned on, for example.

In step S11 depicted in FIG. 9, the mode setting block 63 sets the processing mode to the manual mode and supplies this information to the state estimation block 64.

In step S12, the recognition block 61 recognizes the input information. Of the input information, the recognition block 61 supplies voice recognition result information, sound volume information, gesture information, and manipulation information to the command block 62. In addition, the recognition block 61 supplies line-of-sight positional information to the command block 62, the state estimation block 64, and the image processing block 66. The recognition block 61 supplies the movement and direction of the head 22A to the command block 62 and the state estimation block 64 as the input information.

In step S13, on the basis of the input information supplied from the recognition block 61, the command block 62 recognizes a command from the operator 22. In step S14, the command block 62 determines whether the type of the recognized command is "mode control" or not.

If the type of the command recognized in step S14 is "mode control," then the command block 62 notifies the mode setting block 63 of that command, upon which the processing goes to step S15. In step S15, in accordance with the command supplied from the command block 62, the mode setting block 63 changes operation modes. The mode setting block 63 supplies the changed mode to the state estimation block 64, upon which the processing goes to step S16.

On the other hand, if the type of the command recognized in step S14 is not found to be "mode control," then the processing goes to step S16.

In step S16, the state estimation block 64 determines the operation mode supplied from the mode setting block 63 is the hands-free mode or not. If the operation mode is found to be the hands-free mode in step S16, then the processing goes to step S17.

In step S17, the control apparatus 15 executes state estimation processing for estimating a state of the operator 22 on the basis of the input information supplied from the recognition block 61. Details of this state estimation processing will be described later with reference to FIG. 10.

In step S18, the command block 62 determines whether the type of the command recognized in step S13 from the operator 22 other than commands of which type is "mode control" is permitted or not. If the type of that command is found to be permitted in step S18, then the command block 62 supplies that command to the control block 65.

Then, in step S19, the control block 65 executes the command supplied from the command block 62, upon which the processing goes to step S20.

On the other hand, if the operation mode is found to be not the hands-free mode in step S16 or if the type of the command from the operator 22 other than commands of which type is "mode control" is found to be not permitted in step S18, then the processing goes to step S20.

In step S20, the control apparatus 15 determines whether or not to turn off the power to the control apparatus 15; for example, the control apparatus 15 determines whether or not a command of powering off the control apparatus 15 has been issued by the operator 22. If the power to the control apparatus 15 is found to be not turned off in step s20, then the processing returns to step S12 so as to repeat the processing of steps S12 through S20.

On the other hand, if the power to the control apparatus 15 is found to be turned off in step S20, the processing is terminated.

Figure 10:
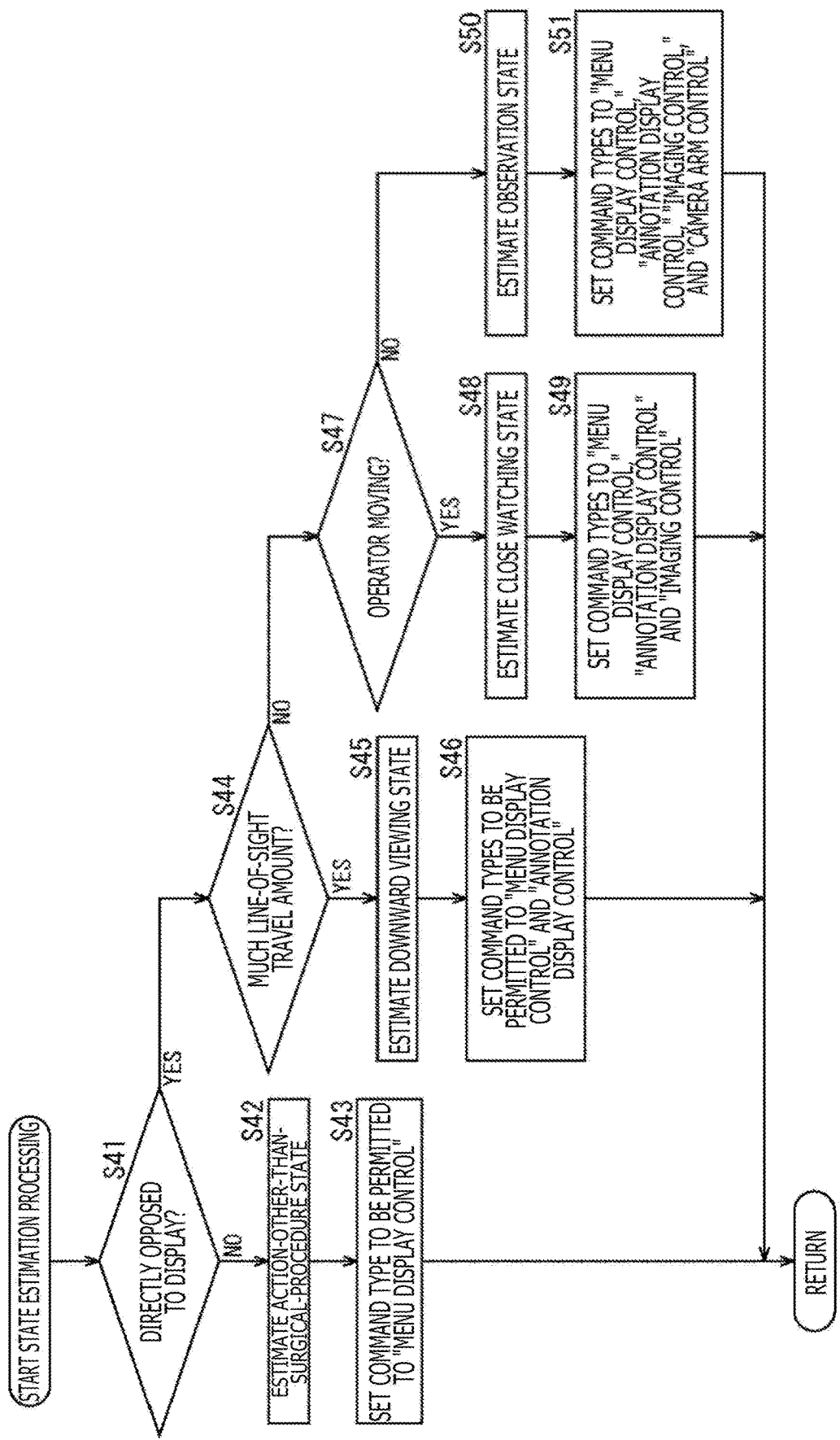
FIG. 10 is a flowchart indicative of details of the state estimation processing depicted in FIG. 9.

FIG. 10 is a flowchart indicative of details of the state estimation processing in step S17 depicted in FIG. 9.

In step S41 depicted in FIG. 10, on the basis of the direction of the head 22A or the line-of-sight positional information in the input information, the state estimation block 64 determines whether the operator 22 is directly opposite to the display 14 or not.

If the operator 22 is found to be not directly opposite to the display 14 in step S41, then the state estimation block 64 estimates that the state of the operator 22 is the action-other-than-surgical-procedure state in step S42, notifying the command block 62 thereof.

In step S43, the command block 62 sets the type of the command from the operator 22 to be permitted other than "mode control" to "menu display control." Then, the processing returns to step S17 depicted in FIG. 9, upon which the processing of step S18 is executed.

On the other hand, if the operator 22 is found to be directly opposite to the display 14 in step S41, the state estimation block 64 determines whether the travel amount of the line of sight is high or not on the basis of the travel amount within a predetermined time of the position indicated by the line-of-sight positional information in step S44.

If the travel amount of the line of sight is found high in step S44, then the state estimation block 64 estimates that the state of the operator 22 is the downward viewing state in step S45, thereby notifying the command block 62 thereof.

In step S46, the command block 62 sets the types of the commands from the operator 22 to be permitted other than "mode control" to "menu display control" and "annotation display control." Then, the processing returns to step S17 depicted in FIG. 9 to repeat the processing of step S18.

Further, if the travel amount of the line of sight is found to be low in step S44, then the state estimation block 64 determines whether the operator 22 is moving or not on basis of the movement of the head 22A in step S47. If the operator 22 is found to be moving in step S47, then the state estimation block 64 estimates that the state of the operator 22 is the close watching state in step S48, thereby notifying the command block 62 thereof.

In step S49, the command block 62 sets the types of the commands from the operator 22 to be permitted other than "mode control" to "menu display control," "annotation display control," and "imaging control." Then, the processing returns to step S17 depicted in FIG. 9 to repeat the processing of step S18.

On the other hand, if the operator 22 is found to be not moving in step S47, then the state estimation block 64 estimates that the state of the operator 22 is the observation state in step S50, thereby notifying the command block 62 thereof.

In step S51, the command block 62 sets the types of the commands from the operator 22 to be permitted to "menu display control," "annotation display control," "imaging control," and "camera arm control." Then the processing returns to step S17 depicted in FIG. 9 to repeat the processing of step S18.

A described above, on the basis of combinations of two or more types of contactless inputs, the surgical system 10 controls the surgical camera 11, the camera arm 12, or the image processing block 66. Therefore, by executing contactless input operations suited for the types of input contents, for example, the operator 22 is able to easily and intuitively control the surgical camera 11, the camera arm 12, and the image processing block 66. That is, the surgical system 10 can realize NUI (Natural User Interface). As a result, the load of the operator 22 is mitigated.

Further, as compared with the case in which the surgical camera 11, the camera arm 12, or the image processing block 66 is controlled by the contactless input of one type, the above-mentioned two or more types of contactless inputs enhance the hit ratio of input recognition, which in turn enhancing the safety of surgical procedures.

Since the surgical system 10 allows the execution of input operations in a contactless manner or by the contact by the leg 22B, the operator 22 himself can execute input operations even if both hands are occupied by the execution of surgical procedure. As a result, as compared with the case in which the operator 22 executes input operations, there is no need for interrupting surgical procedure because of input operations, thereby saving the surgical time. In addition, as compared with the case in which a person other than the operator 22 executes input operations, the surgical system 10 allows the operator 22 execute control as intended by the operator 22, thereby mitigating the load of the operator 22.

Further, the surgical system 10 can restrict the execution of commands issued by the operator 22 in accordance with a state of the operator 22 so as to real failsafe, thereby preventing the control operations that are not intended by the operator 22 due to the erroneous recognition of a command from the operator 22. Consequently, the safety of surgical procedure is enhanced.

Still further, since the surgical system 10 can change the operation mode from the hands-free mode to the manual mode, if a control operation that is not intended by the operator 22 is executed due to the erroneous recognition of a command from the operator 22, the unintended control operation can be stopped.

Second Embodiment (Example of Configuration of Second Embodiment of Surgical System)

Figure 11:
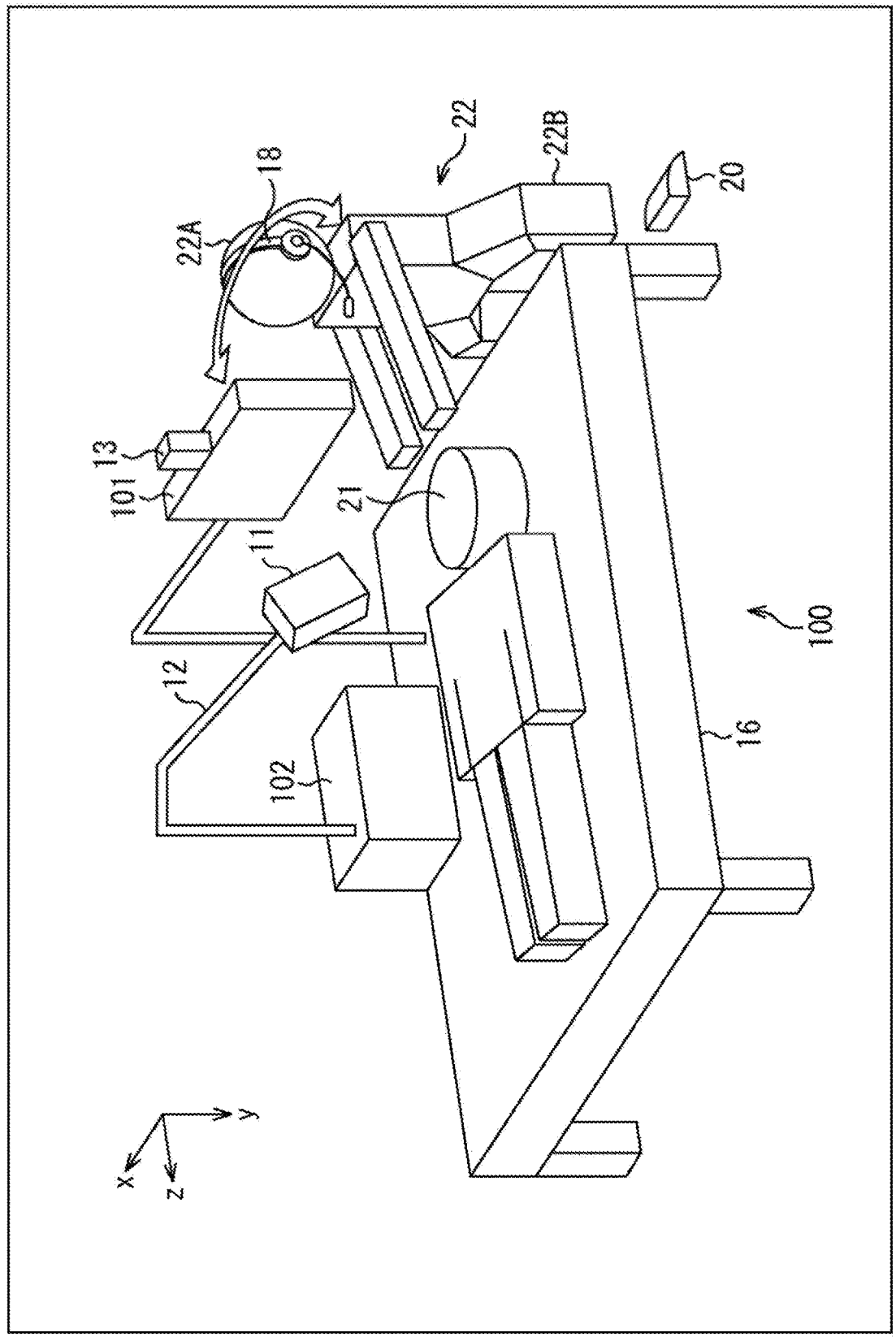
FIG. 11 is a block diagram illustrating one example of a configuration of a surgical system practiced as a second embodiment to which the present disclosure is applied.
Figure 12:
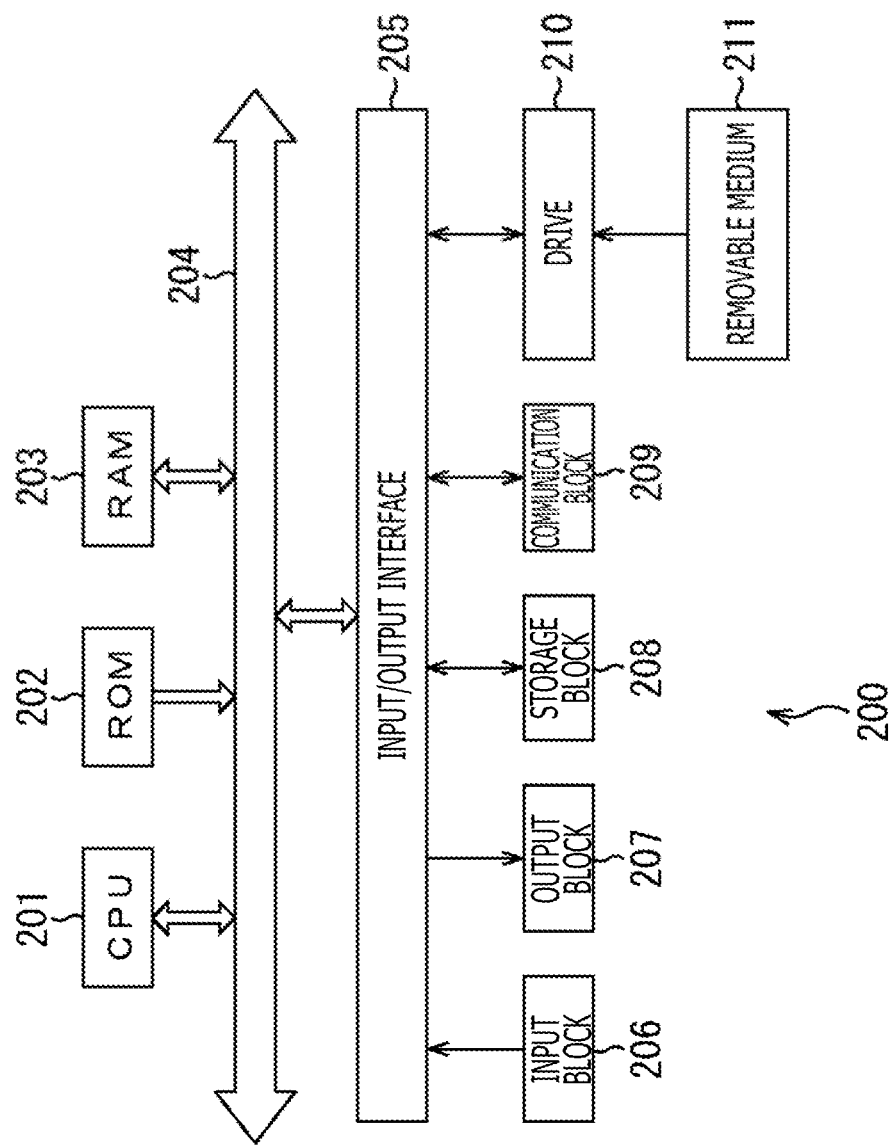
FIG. 12 is a block diagram illustrating one example of a configuration of hardware of a computer.

FIG. 11 is a block diagram illustrating one example of a configuration of a second embodiment of a surgical system to which the present disclosure is applied.

With the configuration depicted in FIG. 11, the configurational components same as those previously described with FIG. 1 are denoted by the same reference symbols. The duplicate description will appropriately skipped.

In configuration, a surgical system 100 depicted in FIG. 11 differs from the surgical system 10 depicted in FIG. 1 in that the surgical system 100 has a display 101 and a control apparatus 102 instead of the display 14 and the control apparatus 15 and does not have the surgical glasses 17 and the marker 19.

With the surgical system 100, the distance between the display 101 and the operator 22 is shorter than the distance between the display 14 and the operator 22, so that the operator 22 recognizes a surgical field image displayed on the display 101 as a 3D image with the naked eyes without using the surgical glasses 17.

To be more specific, the display 101 of the surgical system 100 is a 3D display having a comparatively small screen and is arranged at a position comparatively near the operator 22 (in the example depicted in FIG. 11, a position on the operating table 16 and near the operator 22). The display 101 displays surgical field images and so on sent from the control apparatus 102. On top of the display 101, the action recognition camera 13 is arranged.

Except for a method of recognizing the line of sight and the movement and direction of the head 22A, the control apparatus 102 operates in the similar manner to the control apparatus 15, so that the following describes only this recognition method. The control apparatus 102 detects the position of the head 22A inside an operator image sent from the action recognition camera 13 so as to recognize the movement and direction of the head 22A. Further, the control apparatus 102 detects the direction of the line of sight of the operator 22 from an operator image so as to recognize the position of the line of sight on the screen of the display 14 on the basis of the detected direction.

It should be noted that, with the surgical system 100, the operator 22 does not use the surgical glasses 17, so that the detection of line of sight is executed by use of an operator image taken with the action recognition camera 13; however, it is also practicable to execute the detection of line of sight by a line-of-sight detection device by making the operator 22 wear the surgical glasses having the line-of-sight detection device.

Further, with the surgical system 100, since the distance between the action recognition camera 13 and the operator 22 is short, the movement and direction of the head 22A are detected from an operator image; however, it is also practicable to for the operator 22 to wear the marker 19 so as to detect the movement and direction of the head 22A from a position of the marker 19 inside an operator image.

Still further, the display 101 may be arranged at a position comparatively far from the operator 22. The display 101 is a 3D display with which the operator 22 can recognize 3D images through 3D polarized glasses, so that the operator 22 may use 3D polarized glasses.

Third Embodiment (Explanation of Computer to which Present Disclosure is Applied)

The above-mentioned sequence of processing operations by the control apparatus 15 (102) can be executed by hardware or software. In the execution of the sequence of processing operations by software, the programs constituting that software are installed on a computer. It should be noted that the computer includes a computer built in dedicated hardware and a general-purse personal computer, for example, in which various programs can be installed for the execution of various functions.

FIG. 12 is a block diagram illustrating one example of the hardware of a computer for executing the above-mentioned sequence of processing operations by programs.

In a computer 200, a CPU (Central Processing Unit) 201, a ROM (Read Only Memory) 202, and a RAM (Random Access Memory) 203 are interconnected by a bus 204.

The bus 204 is further connected with an input/output interface 205. The input/output interface 205 is connected with an input block 206, an output block 207, a storage block 208, a communication block 209, and a drive 210.

The input block 206 includes a keyboard, a mouse, a microphone, and so on. The output block 207 includes a display, a speaker, and so on. The storage block 208 includes a hard disk drive, a nonvolatile memory, and so on. The communication block 209 includes a network interface and so on. The drive 210 drives a removable medium 211 such as a magnetic disc, an optical disc, a magneto-optical disc, or a semiconductor memory.

With the computer 200 configured as described above, the CPU 201 loads programs from the storage block 208 into the RAM 203 via the input/output interface 205 and the bus 204 and executes the loaded programs so as to execute the above-mentioned sequence of processing operations.

Programs to be executed by the computer 200 (the CPU 201) may be provided as recorded to the removable medium 211 that is a package medium or the like. In addition, programs may be provided through a wired or wireless transmission medium, such as a local area network, the Internet, or digital satellite broadcasting.

With the computer 200, programs can be installed in the storage block 208 via the input/output interface 205 by loading the removable medium 211 on the drive 210. In addition, programs can be installed in the storage block 208 by receiving by the communication block 209 the programs via a wired or wireless transmission medium. Otherwise, programs can be installed in the ROM 202 or the storage block 208 in advance.

It should be noted that programs to be executed by the computer 200 may be programs in which processing is executed in a time sequence manner by following the sequence described in the present description or in a parallel manner or on an on-demand basis with required timings.

In the present description, a system denotes an aggregation of two or more configurational components (apparatuses, modules (parts), etc.) regardless whether all the configurational components are within a same housing or not. Therefore, two or more apparatuses accommodated in separate housings and interconnected via a network are a system or one apparatus with two or more modules accommodated in one housing is also a system.

It should be noted that the effects described here are not necessarily restricted; namely, any of the effects described in the present disclosure may be effects denoted here.

While preferred embodiments of the present disclosure are not limited to the embodiments described above and variations may be made without departing from the gist of the present disclosure.

For example, in the first embodiment through the third embodiment, the control apparatus 15 (102) executes control operations on the basis of two or more types of contactless input combinations and the control operations are restricted in accordance with states of the operator 22, both thereby enhancing the safety of surgical procedure; however, it is also practicable to use only one of the above-mentioned measures so as to enhance the safety of surgical procedure.

Further, targets of the restriction by the control apparatus 15 (102) may be anything as far as the targets are surgical apparatuses. For example, the control apparatus 15 (102) can also control such surgical imaging apparatuses as endoscopes and video microscopes.

Moreover, it is also practicable for zoom control to be realized not by the imaging control of the surgical camera 11 but by processing a surgical field image in the image processing block 66.

In this case, in accordance with a zoom-in imaging command, the image processing block 66 enlarges a surgical field image sent from the surgical camera 11 so as to execute electronic zooming in which a zoom-in image taken in a zoom-in manner around a subject corresponding to the position of line of sight is generated from the surgical field image. Likewise, in accordance with a zoom-out imaging command, the image processing block 66 reduces a surgical field image sent from the surgical camera 11 so as to generate a zoom-out image taken in a zoom-out manner around a subject corresponding to the position of line of sight from the surgical field image. It should be noted that, at this moment, on the basis of the line-of-sight positional information, the image processing block 66 may superimpose a marker on the position corresponding to the line of sight inside the zoom-in image or the zoom-out image.

Further, while a surgical field image is displayed on the display 14, annotation display may be always executed. The contactless inputs are not restricted to the voice and line of sight of the operator 22, the movement and direction of the head 22A, and the gesture of the operator 22. For example, the contactless inputs may include the movement and attitude of other than the head 22A of the operator 22.

The means of accepting contactless inputs may be wearable like the surgical glasses 17 and the microphone 18 or may not be wearable.

Even if the operation mode is the manual mode, the control apparatus 15 (102) may estimate a state of the operator 22 and, in accordance with the estimated state, restrict the control of the surgical camera 11, the camera arm 12, and the image processing block 66.

It should be noted that the present disclosure can also take the following configurations.

(1)

A surgical control apparatus including:

a state estimation block configured to estimate, on the basis of at least one type of contactless input from a user recognized by a first contactless input recognition block, a state of the user; and a restriction block configured to restrict, in accordance with the state estimated by the state estimation block, a control operation of a surgical apparatus based on at least one type of contactless input from the user recognized by a second contactless input recognition block.

(2)

The surgical control apparatus according to (1) above, in which the contactless input is a voice, a line of sight, a movement, or a gesture of the user.

(3)

The surgical control apparatus according to (1) or (2) above, in which the control operation is executed on the basis of at least one type of contactless input from the user recognized by the second contactless input recognition block and an input by contact from the user recognized by a contact input recognition block.

(4)

The surgical control apparatus according to any one of (1) through (3) above, in which the state estimation block estimates a state of the user as an action-other-than-surgical-procedure state, a downward viewing state, a close watching state, or an observation state.

(5)

The surgical control apparatus according to (4) above, in which a control operation of the surgical apparatus is a menu display control operation of a display control apparatus, an annotation display control operation of a display control apparatus, an imaging control operation of a surgical imaging apparatus for taking a surgical field image, or an arm driving control operation for holding the surgical imaging apparatus.

(6)

The surgical control apparatus according to (5) above, in which if a state of the user is estimated by the state estimation block to be an action-other-than-surgical-procedure state, the restriction block restricts the control operation of the surgical apparatus to the menu display control operation of the display control apparatus.

(7)

The surgical control apparatus according to (5) or (6) above, in which if a state of the user is estimated by the state estimation block to be a downward viewing state, the restriction block restricts the control operation of the surgical apparatus to the annotation display control operation of the display control apparatus.

(8)

The surgical control apparatus according to any one of (5) through (7) above, in which if a state of the user is estimated by the state estimation block to be a close watching state, the restriction block restricts the control operation of the surgical apparatus to the imaging control operation of the surgical imaging apparatus.

(9)

The surgical control apparatus according to any one of (5) through (8) above, in which if a state of the user is estimated by the state estimation block to be an observation state, the restriction block restricts the control operation of the surgical apparatus to the driving control operation of the arm.

(10)

The surgical control apparatus according to any one of (1) through (9) above, further including:

a mode setting block configured to set an operation mode of the surgical control apparatus on the basis of at least one type of contactless input from the user recognized by the second contactless input recognition block.

(11)

The surgical control apparatus according to (10) above, in which the state estimation block estimates the state if the operation mode is a mode for controlling the surgical apparatus on the basis of at least one type of contactless input from the user.

(12)

A surgical control method including:

a state estimation step of estimating, on the basis of at least one type of contactless input from a user recognized by a first contactless input recognition block, a state of the user; and a restriction step of restricting, in accordance with the state estimated by processing in the state estimation step, a control operation of a surgical apparatus based on at least one type of contactless input from the user recognized by a second contactless input recognition block;

these steps being executed by a surgical control apparatus.

(13)

A program for having a computer function as:

a state estimation block configured to estimate, on the basis of at least one type of contactless input from a user recognized by a first contactless input recognition block, a state of the user; and a restriction block configured to restrict, in accordance with the state estimated by the state estimation block, a control operation of a surgical apparatus based on at least one type of contactless input from the user recognized by a second contactless input recognition block.

REFERENCE SIGNS LIST

11 . . . Surgical camera, 12 . . . Camera arm, 15 . . . Control apparatus, 62 . . . Command block, 63 . . . Mode setting block, 64 . . . State estimation block, 66 . . . Image processing block, 71 . . . Voice recognition block, 72 . . . Line-of-sight recognition block, 73 . . . Head recognition block, 74 . . . Gesture recognition block, 75 . . . Manipulation recognition block

The invention claimed is:

1. A surgical control apparatus comprising:
circuitry configured to
recognize a first type of contactless input from a user as first input information;
recognize a second type of contactless input from the user as second input information, the second type of contactless input being different from the first type of contactless input;
estimate a state of the user from a plurality of predetermined user states, on the basis of the first input information and the second input information;
set at least one command type from a plurality of command types as a permitted command type and set other commands from the plurality of command types as restricted command type, in accordance with the state of the user estimated, the at least one permitted command type including one or more commands for controlling a control operation of a surgical apparatus, each command having an associated recognition condition; and
output one of the one or more commands on the basis of whether the first input information and the second input information satisfy a recognition condition of one of the one of the one or more commands.

2. The surgical control apparatus according to claim 1, wherein
the first and second types of contactless input include a voice input, a line of sight input, a movement input, or a gesture input of the user.

3. The surgical control apparatus according to claim 1, wherein
the control operation is executed on the basis of the first and second types of contactless input from the user recognized by the second contactless input recognition circuit and an input by contact from the user recognized by a contact input recognition circuit.

4. The surgical control apparatus according to claim 1, wherein
the circuitry is configured to estimate the state of the user as an action-other-than-surgical-procedure state, a downward viewing state, a close watching state, or an observation state.

5. The surgical control apparatus according to claim 4, wherein
the control operation of the surgical apparatus includes a menu display control operation of a display control apparatus, an annotation display control operation of a display control apparatus, an imaging control operation of a surgical imaging apparatus for taking a surgical field image, and an arm driving control operation for holding the surgical imaging apparatus.

6. The surgical control apparatus according to claim 5, wherein
if the state of the user is estimated to be an action-other-than-surgical-procedure state, the circuitry is configured to restrict set the command type for controlling the menu display control operation of the display control apparatus as the permitted command type.

7. The surgical control apparatus according to claim 5, wherein
if the state of the user is estimated to be a downward viewing state, the circuitry is configured to set the command type for controlling operation of the annotation display control operation of the display control apparatus as the permitted command type.

8. The surgical control apparatus according to claim 5, wherein
if the state of the user is estimated to be a close watching state, the circuitry is configured to set the command type for controlling operation of the imaging control operation of the surgical imaging apparatus as the permitted command type.

9. The surgical control apparatus according to claim 5, wherein
if the state of the user is estimated to be an observation state, the circuitry is configured to restrict the command type for controlling operation of the driving control operation of an arm for holding the surgical imaging apparatus as the permitted command type.

10. The surgical control apparatus according to claim 1, wherein
the circuitry is configured to estimate the state of the user if the operation mode is a mode for controlling the surgical apparatus on the basis of at least one type of contactless input from the user.

11. A surgical control method comprising:
recognizing a first type of contactless input from a user as first input information;
recognizing a second type of contactless input from the user as second input information, the second type of contactless input being different from the first type of contactless input;
estimating a state of the user, from a plurality of predetermined user states, on the basis of the first input information and the second input information;
setting, in accordance with the state of the user estimated, at least one command type from a plurality of command types as a permitted command type and set other commands from the plurality of command types as restricted command type, the at least one command type including one or more commands for controlling a control operation of a surgical apparatus, each command having an associated recognition condition; and outputting one of the one or more commands on the basis of whether the first input information and the second input information satisfy a recognition condition of one of the one of the one or more commands.

12. A non-transitory computer readable medium having stored thereon a program that, when executed by a computer, causes the computer to execute processing, the processing comprising:
recognizing a first type of contactless input from a user as first input information;
recognizing a second type of contactless input from the user as second input information, the second type of contactless input being different from the first type of contactless input;
estimating a state of the user, from a plurality of predetermined user states, on the basis of the first input information and the second input information;
setting, in accordance with the state of the user estimated, at least one command type from a plurality of command types as a permitted command type and set other commands from the plurality of command types as restricted command type, the at least one command type including one or more commands for controlling a control operations of a surgical apparatus, each command having an associated recognition condition; and
outputting one of the one or more commands on the basis of whether the first input information and the second input information satisfy a recognition condition of one of the one of the one or more commands.

13. The surgical control apparatus according to claim 1, wherein, the circuitry is configured to set the command type to at least one of a menu display control, an annotation display control, an imaging control, and a camera arm control as permitted command types.

14. The surgical control apparatus according to claim 13, wherein, when the state of the user indicates the user is not looking at a display, the circuitry is configured to set the command type to the menu display control as the permitted command type.

15. The surgical control apparatus according to claim 13, wherein, when the state of the user indicates the user is looking at a display, the circuitry is configured to set the menu display control and the annotation display control as permitted command types.

16. The surgical control apparatus according to claim 1, wherein, when the command type is a camera arm control for holding a surgical imaging apparatus, the circuitry is configured to set the command types for controlling operation based on at least one type of contactless input from the user recognized by a third contactless input recognition.

17. The surgical control apparatus according to claim 16, wherein the circuitry is configured to set the command type for controlling a camera arm to change imaging angles without changing an imaging center when line-of-sight information of the user is unchanged and the user travels as the permitted command type.

18. The surgical control apparatus according to claim 16, wherein the circuitry is configured to set the command type for controlling a camera arm to change an imaging center when line-of-sight information of the user and the user rotates as the permitted command type.

19. The surgical control apparatus according to claim 3, wherein, the circuitry is configured to set the command type for controlling the operation to at least one of a menu display control, an annotation display control, and a camera arm control as the permitted command type based on the input by contact from the user recognized by a contact input recognition circuit.

20. The surgical control apparatus according to claim 1, wherein, when the second contactless input recognition circuit recognizes a gesture by the user that is not a registered gesture or recognizes a volume of the user is greater than a predetermined value, the circuitry is configured to determine an emergency state.

* * * * *